(12) United States Patent
Kroll et al.

(10) Patent No.: US 9,272,150 B2
(45) Date of Patent: Mar. 1, 2016

(54) METHOD FOR DETECTING AND LOCALIZING INSULATION FAILURES OF IMPLANTABLE DEVICE LEADS

(71) Applicant: Lambda Nu Technology LLC, Orono, MN (US)

(72) Inventors: Mark William Kroll, Crystal Bay, MN (US); Charles Dennis Swerdlow, Los Angeles, CA (US)

(73) Assignee: Lambda Nu Technology LLC, Orono, MN (US)

( * ) Notice: Subject to any disclaimer, the term of this patent is extended or adjusted under 35 U.S.C. 154(b) by 0 days.

(21) Appl. No.: 13/833,477

(22) Filed: Mar. 15, 2013

(65) Prior Publication Data

US 2013/0325079 A1    Dec. 5, 2013

Related U.S. Application Data

(60) Provisional application No. 61/689,189, filed on Jun. 1, 2012.

(51) Int. Cl.
| | |
|---|---|
| *A61N 1/37* | (2006.01) |
| *A61N 1/39* | (2006.01) |
| *A61B 5/0424* | (2006.01) |
| *A61B 5/053* | (2006.01) |
| *A61N 1/08* | (2006.01) |
| *A61B 5/00* | (2006.01) |

(52) U.S. Cl.
CPC ............ *A61N 1/37* (2013.01); *A61B 5/0424* (2013.01); *A61B 5/0538* (2013.01); *A61N 1/3925* (2013.01); *A61B 5/686* (2013.01); *A61B 2560/0276* (2013.01); *A61N 2001/083* (2013.01)

(58) Field of Classification Search
CPC ............................. A61N 1/37; A61N 1/3925
USPC ................................ 607/5, 63, 115
See application file for complete search history.

(56) References Cited

U.S. PATENT DOCUMENTS

| | | | |
|---|---|---|---|
| 3,599,055 | A | 8/1971 | Bloom |
| 4,766,549 | A | 8/1988 | Schweitzer, III et al. |
| 5,003,975 | A | 4/1991 | Hafelfinger et al. |
| 5,231,987 | A | 8/1993 | Robson |
| 5,243,980 | A | 9/1993 | Mehra |

(Continued)

FOREIGN PATENT DOCUMENTS

| | | |
|---|---|---|
| EP | 0288630 B1 | 11/1988 |
| EP | 2032027 B1 | 10/2011 |

OTHER PUBLICATIONS

"Agilent Impedance Measurement Handbook A Guide to Measurement Technology and Techniques 4th Edition," Agilent Technologies, Inc., Jun. 17, 2009, 140 pages.

(Continued)

*Primary Examiner* — Christopher A Flory
(74) *Attorney, Agent, or Firm* — Patterson Thuente Pedersen, P.A.

(57) ABSTRACT

The invention relates to a method and apparatus for diagnosis of conductor anomalies, such as insulation failures, in an implantable medical device, such as an implantable cardioverter defibrillator (ICD), a pacemaker, or a neurostimulator. Insulation failures are detected and localized by identifying changes in electrical fields via surface (skin) potentials. Small variations in potential are detected along the course of the electrode near the site of insulation failure.

15 Claims, 12 Drawing Sheets

(56) References Cited

U.S. PATENT DOCUMENTS

| | | | |
|---|---|---|---|
| 5,361,776 | A | 11/1994 | Samuelson et al. |
| 5,405,363 | A | 4/1995 | Kroll et al. |
| 5,741,311 | A | 4/1998 | McVenes et al. |
| 5,755,742 | A | 5/1998 | Schuelke et al. |
| 5,897,577 | A | 4/1999 | Cinbis et al. |
| 5,944,746 | A | 8/1999 | Kroll |
| 6,104,954 | A | 8/2000 | Blunsden |
| 6,317,633 | B1* | 11/2001 | Jorgenson et al. ............. 607/28 |
| 6,445,951 | B1 | 9/2002 | Mouchawar |
| 6,490,486 | B1 | 12/2002 | Bradley |
| 6,928,325 | B2 | 8/2005 | Zhu et al. |
| 7,047,083 | B2 | 5/2006 | Gunderson et al. |
| 7,081,130 | B2 | 7/2006 | Jang |
| 7,120,563 | B2 | 10/2006 | Bechhoefer et al. |
| 7,289,851 | B2 | 10/2007 | Gunderson et al. |
| 7,369,893 | B2 | 5/2008 | Gunderson |
| 7,454,249 | B1 | 11/2008 | Bornzin et al. |
| 7,747,320 | B1 | 6/2010 | Kroll et al. |
| 7,764,998 | B1 | 7/2010 | Raddatz |
| 8,200,330 | B2 | 6/2012 | Kroll et al. |
| 8,352,033 | B2 | 1/2013 | Kroll |
| 8,463,384 | B2 | 6/2013 | Germanson et al. |
| 8,467,872 | B2 | 6/2013 | Hareland |
| 8,577,457 | B2 | 11/2013 | Miller et al. |
| 8,644,932 | B2 | 2/2014 | Seifert et al. |
| 8,700,156 | B2* | 4/2014 | Kroll ............................. 607/28 |
| 8,812,103 | B2 | 8/2014 | Kroll et al. |
| 8,825,158 | B2 | 9/2014 | Swerdlow |
| 2003/0004552 | A1* | 1/2003 | Plombon et al. ................ 607/27 |
| 2004/0010303 | A1 | 1/2004 | Bolea et al. |
| 2004/0068301 | A1 | 4/2004 | Waltman et al. |
| 2004/0158290 | A1 | 8/2004 | Girouard et al. |
| 2005/0137636 | A1* | 6/2005 | Gunderson et al. ............. 607/27 |
| 2005/0187586 | A1 | 8/2005 | David et al. |
| 2005/0256547 | A1 | 11/2005 | Stahmann et al. |
| 2006/0135886 | A1 | 6/2006 | Lippert et al. |
| 2006/0241513 | A1 | 10/2006 | Hatlestad |
| 2006/0265038 | A1 | 11/2006 | Hagen et al. |
| 2007/0208387 | A1 | 9/2007 | Mower |
| 2008/0208271 | A1 | 8/2008 | Sih et al. |
| 2008/0309351 | A1 | 12/2008 | Stewart et al. |
| 2009/0099615 | A1 | 4/2009 | Kroll |
| 2009/0292331 | A1 | 11/2009 | Gunderson et al. |
| 2009/0306735 | A1 | 12/2009 | Lagercrantz et al. |
| 2010/0179446 | A1* | 7/2010 | Bojovic et al. ................ 600/512 |
| 2010/0228307 | A1 | 9/2010 | Kroll et al. |
| 2011/0054554 | A1 | 3/2011 | Swerdlow |
| 2011/0054556 | A1 | 3/2011 | Swerdlow |
| 2011/0054558 | A1 | 3/2011 | Gunderson et al. |
| 2011/0160808 | A1* | 6/2011 | Lyden et al. ..................... 607/63 |
| 2011/0160829 | A1 | 6/2011 | Foster et al. |
| 2012/0035491 | A1 | 2/2012 | Mahajan et al. |
| 2012/0191153 | A1* | 7/2012 | Swerdlow et al. ................ 607/8 |
| 2012/0197331 | A1* | 8/2012 | Germanson et al. ............ 607/11 |
| 2012/0197365 | A1* | 8/2012 | Germanson et al. .......... 607/116 |
| 2013/0013038 | A1* | 1/2013 | Miller .......................... 607/116 |
| 2013/0123871 | A1 | 5/2013 | Kroll |
| 2013/0304139 | A1 | 11/2013 | Musley et al. |
| 2013/0304160 | A1 | 11/2013 | Gunderson et al. |
| 2013/0325080 | A1 | 12/2013 | Kroll et al. |
| 2014/0155947 | A1 | 6/2014 | Kroll et al. |
| 2014/0324123 | A1 | 10/2014 | Kroll et al. |
| 2014/0371831 | A1 | 12/2014 | Swerdlow |
| 2015/0005862 | A1 | 1/2015 | Kroll et al. |
| 2015/0088213 | A1 | 3/2015 | Kroll et al. |
| 2015/0151118 | A1 | 6/2015 | Kroll et al. |

OTHER PUBLICATIONS

Armour, Andrew J., et al., "Gross and Microscopic Anatomy of the Human Intrinsic Cardiac Nervous System," Anatomical Record, 1997, pp. 289-298.

Balkhy, Husam H., et al., "Autonomic Ganglionated Plexi: Characterization and Effect of Epicardial Microwave Ablation in a Canine Model of Vagally Induced Actue Atrial Fibrillation," Meeting for the International Society for Minimally Invasive Cardiothoracic Surgery (Abstract), 2006.

Brewer et al., "Low Voltage Shocks Have a Significantly Higher Tilt of the Internal Electric Field Than Do High Voltage Shocks," Angeion Corporation, Jan. 1995, Part II, PACE, vol. 18, pp. 214-220.

Chevalier, P., "Quantitative Study of Nerves of the Human Left Atrium," Heart Rhythm, 2005, pp. 518-522.

Dilling-Boer, Dagmara et al., "Ablation of Focally Induced Atrial Fibrillation: Selective or Extensive?," J. Cardio. Electryphys., 2004, pp. 200-205.

Haissaguerre, Michel et al., "Pulmonary Veins in the Substrate for Atrial Fibrillation: The "venous wave" Hypothesis," 2004, pp. 2290-2292.

Haissaguerre, Michel et al., "Spontaneous Initiation of Atrial Fibrillation by Ecoptic Beats Originating in the Pulmonary Veins," NEJM, 2006, pp. 659-666.

Kilgore, K.L., et al., "Nerve Conduction Block Utilising High-Frequency Alternating Current," Med. Biol. Eng. Comput., 2004, pp. 394-406.

Kumagai, K., et al., "Electrophysiologic Properties of Pulmonary Veins Assessed Using a Multielectrode Basket Catheter," 2004, pp. 2281-2289.

Levy, S., "Characterization of Different Subsets of Atrial Fibrillation in General Practice in France: The ALFA Study," The College of French Cardiologists, Circulation, 1999, pp. 3028-3035.

Lo et al., "Noise-Domain Reflectometry for Locating Wiring Faults," IEEE Transactions on Electromagnetic Compatibility, vol. 47, No. 1, Feb. 2005.

Nathan, H., et al., "The Junction Between the Left Atrium and the Pulmonary Veins: An Anatomic Study of Human Hearts," Circulation, 1966, pp. 412-422.

Oh., S., "Vagal Denervation and Atrial Fibrillation Inducibility: Epicardial Fat Pad Ablation Does Not Have Long-Term Effects," Heart Rhythm, 2006, pp. 701-708.

Oral, Hakan et al., "Pulmonary Vein Isolation for Paroxysmal and Persistent Atrial Fibrillation," Circulation, 2002, pp. 1077-1081.

Pappone, Carlo, "Pulmonary Vein Denervation Enhances Long-Term Benefit After Circumferential Ablation for Paroxysmal Atrial Fibrillation," Circulation, 2004, pp. 327-334.

Patterson, E. et al., "Triggered Firing in Pulmonary Veins Initiated by In Vitro autonomic nerve stimulation," Heart Rhythm, 2005, pp. 624-631.

Patterson, Eugene et al., "Sodium-Calcium Exchange Initiated by the Ca2+ Transient: An Arrhythimia Trigger Within Pulmonary Veins," J. Am. Coll. Cardiol, 2006, pp. 1196-1206.

Po Sunny S., et al., "Rapid and Stable Re-entry within the Pulmonary Vein as a Mechanism Initiating Paroxysmal Atrial Fibrillation," J.Am Coll. Cariol., 2005, pp. 1871-1877.

Po, Sunny S. et al., "Experimental Model for Paroxysmal Atrial Fibrillation Arising at the Pulmonary Vein-Atrial Junctions," Heart Rhythm, 2006, pp. 201-208.

Randall, David C., et al., "Ablation of Posterior Atrial Ganglionated Plexus Potentiates Sympathetic Tachycardia to Behavioral Stress," Comp. Physiol., 1998, pp. 779-787.

Schauerte, P., et al., "Ventricular Rate Control During Atrial Fibrillation by Cardiac Parasympathetic Nerve Stimulation: A Transvenous Approach," J. Am. Coll. Cardiol., 1999, pp. 2043-2050.

Schauerte, Patrick et al., "Catheter Ablation of Cardiac Autonomic Nerves for Prevention of Vagal Atrial Fibrillation," Circulation, 2000, pp. 2774-2780.

Schauerte, Patrick, "Focal Atrial Fibrillation: Experimental Evidence for a Pathophysiologic Role of the Autonomic Nervous System," Cardiovasc Electrophysiol., 2001, pp. 592-599.

Scherlag, Benjamin J., et al., "Autonomically Induced Conversion of Pulmonary Vein Focal Firing Into Atrial Fibrillation," J. Am Coll. Cardiol., 2005, pp. 1878-1886.

Scherlag, Benjamin, "Electrical Stimulation to Identify Neural Elements on the Heart: Their Role in Atrial Fibrillation," J. Interv. Card, Electrophysiol, 2005, pp. 37-42.

Tai, C., "Stimulation Analysis of Conduction Block in Unmyelinated Axons Induced by High-Frequency Biphasic Electrical Currents," IEEE T-BME, 2005, p. 1323.

(56) References Cited

OTHER PUBLICATIONS

Tchou et al., "The AngeMed Sentinel Implantable Antitachycardia Pacer Cardioverter-Defibrillator," Implantable Cardioverter-Defibrillators: A Comprehensive Textbook, Copyright 1994, pp. 755-761.

Tomasic, "Acute and Chronic High-Frequency Properties of Cardiac Pacing and Defibrillation Leads," Med Biol Eng Comput 50:827-837, 2012.

Ellenbogen, "Performance of ICD Lead Integrity Alert to Assist in the Clinical Diagnosis of ICD Lead Failures: Analysis of Different ICD Leads," Circulation Arrhythmia and Electrophysiology, Oct. 7, 2013.

Swerdlow, "Downloadable Algorithm to Reduce Inappropriate Shocks Caused by Fractures of Implantable Cardioverter-Defibrillator Leads," Circulation Journal of the American Heart Association, Nov. 3, 2008, 9 pages.

Swerdlow, "Downloadable Software Algorithm Reduces Inappropriate Shocks Caused by Implantable Cardioverter-Defibrillator Lead Fractures—A Prospective Study," Circulation Journal of the American Heart Association, Sep. 27, 2010, 8 pages.

PCT Application No. PCT/US2013/043386, filed May 30, 2013, Search Report and Written Opinion dated Sep. 27, 2013, 10 pages.

PCT Application No. PCT/US2013/043389, filed May 30, 2013, Search Report and Written Opinion dated Sep. 5, 2013, 9 pages.

Application and File history for U.S. Appl. No. 12/868,056, filed Aug. 25, 2010. Inventor Swerdlow.

Application and File history for U.S. Appl. No. 13/735,599, filed Jan. 7, 2013. Inventor Kroll.

Application and File history for U.S. Appl. No. 13/842,838, filed Mar. 15, 2013. Inventor Kroll.

Application and File history for U.S. Appl. No. 12/252,310, filed Oct. 15, 2008. Inventor: Kroll.

Application and File history for U.S. Appl. No. 13/843,145, filed Mar. 15, 2013. Inventors: Kroll et al.

Application and File history for U.S. Appl. No. 14/224,876, filed Mar. 25, 2014. Inventors: Kroll et al.

Application and File history for U.S. Appl. No. 14/224,281, filed Mar. 25, 2014. Inventors: Kroll et al.

Application and File history for U.S. Appl. No. 14/203,688, filed Mar. 11, 2014. Inventors: Kroll et al.

Application and File history for U.S. Appl. No. 14/224,335, filed Mar. 25, 2014. Inventors: Kroll et al.

Application and File history for U.S. Appl. No. 14/453,679, filed Aug. 7, 2014. Inventors: Kroll et al.

Application and File history for U.S. Appl. No. 14/472,027, filed Aug. 28, 2014. Inventors: Kroll et al.

PCT Application No. PCT/US2013/072957, Filed Dec. 4, 2013, Search Report and Written Opinion dated Mar. 6, 2014.

PCT Application No. PCT/US2015/022435, Filed Mar. 25, 2015, Search Report and Written Opinion dated Jun. 27, 2015.

* cited by examiner

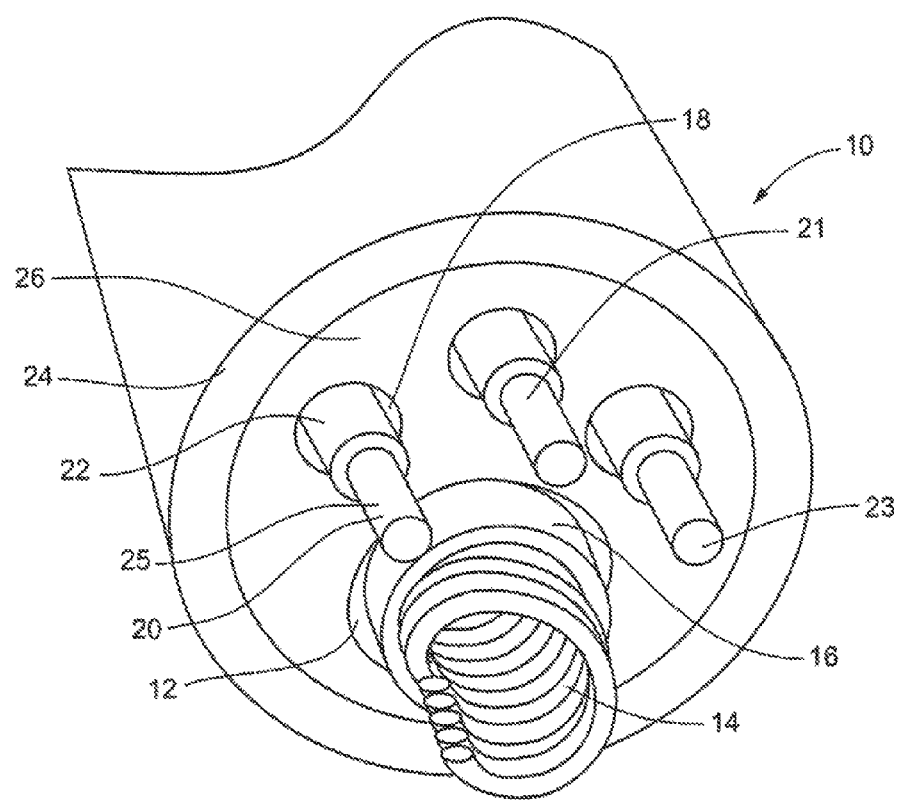

METHOD FOR DETECTING AND LOCALIZING INSULATION FAILURES OF IMPLANTABLE DEVICE LEADS

RELATED APPLICATION

The present application claims the benefit of U.S. Provisional Application No. 61/689,189 filed Jun. 1, 2012, which is incorporated herein in its entirety by reference.

FIELD OF THE INVENTION

The present invention relates, generally, to scientific and medical systems, apparatus and methods. More particularly, the invention relates to method and apparatus for diagnosis of conductor anomalies. Most particularly, the invention relates to a method and apparatus for diagnosis of conductor anomalies, such as insulation failures, in an implantable medical device, such as an implantable cardioverter defibrillator (ICD), a pacemaker, or a neurostimulator. Insulation failures are detected and localized by identifying changes in electrical fields via surface (skin) potentials. Small variations in potential are detected along the course of the electrode near the site of insulation failure.

BACKGROUND

The long-term reliability and safety of implantable cardiac leads is a significant issue. Anomalies of conductors in implantable medical devices constitute a major cause of morbidity. Representative examples of such medical devices include, but are not limited to, pacemakers, vagal nerve stimulators, pain stimulators, neurostimulators, and implantable cardioverter defibrillators (ICDs). For example, early diagnosis of ICD lead conductor anomalies is important to reduce morbidity and/or mortality from loss of pacing, inappropriate ICD shocks, and/or ineffective treatment of ventricular tachycardia or fibrillation (ventricular fibrillation). The early diagnosis of conductor anomalies for implantable cardiac leads is a critically important step in reducing these issues and making ICDs safer.

Multilumen ICD defibrillation electrodes or leads include one or more high-voltage conductors and one or more pace-sense conductors. The leads can be implanted as subcutaneous or intravascular leads. Insulation failures have been known to result in functional failure of the corresponding conductor. Functional failure of a pace-sense conductor may result in symptoms caused by loss of pacing functions for bradycardia, cardiac resynchronization, or antitachycardia pacing. Functional failure of a high-voltage conductor may result in fatal failure of cardioversion or defibrillation.

Thus, one major goal is high sensitivity of diagnosis: identification of lead insulation failures at the subclinical stage, before they present as a clinical problem. A second major goal is high specificity: a false positive provisional clinical diagnosis of lead insulation failure may trigger patient anxiety and lead to potentially-avoidable diagnostic testing. A false positive clinical diagnosis of insulation failure results in unnecessary lead replacement, with corresponding expense and surgical risk.

Insulation failures occur most commonly at three regions along the course of a pacemaker or ICD lead. The first region is within the pocket, caused either by abrasion of the lead insulation by pressure from the housing ("CAN") of the pulse generator or twisting of the lead within the pocket. The second region is that between the clavicle and first rib, where the lead is subject to "clavicular crush." The third region is the intracardiac region near the tricuspid valve. This third region is a particularly common site of insulation failure for the St. Jude Riata® lead which is subject to "inside-out" insulation failure due to motion of the internal cables relative to the outer insulation.

It is extremely difficult to detect and localize lead insulation failures on an ICD implanted in the chest of a patient. The taking of x-rays has been attempted to easily identify anomalies but has had extremely limited success, and essentially zero success where the anomaly is a lead insulation failure. For example, FIG. 1 is an x-ray of an implanted ICD, the arrow showing a small area of insulation stress from a tight suture (taken from Radiography of Cardiac Conduction Devices: A Comprehensive Review by Amanda L. Aguilera, M D, Yulia V. Volokhina, D O and Kendra L. Fisher, M D, October 2011 RadioGraphics, 31, 1669-1682). Whether this area of insulation stress has already led to an insulation failure or not is impossible to discern from this image.

Due to the failure of x-ray diagnosis, the primary method in the prior art for monitoring pacemaker and ICD lead integrity is periodic measurement of electrical resistance, usually referred to as "impedance monitoring." Impedance monitoring uses single pulses. Various methods well-known in the art provide a measure of impedance close to the direct-current resistance.

However, another common issue is that insulation failures commonly present clinically without detected changes in impedance as measured by presently used methods. There are several possible explanations. One explanation is that the range of impedance in normally functioning leads may be wide. For example, it has been reported that high-voltage impedance in normally functioning high-voltage leads may fall approximately 30% from maximum measured values (Gunderson B D, Ellenbogen K A, Sachanandani H, Wohl B N, Kendall K T, Swerdlow C D. Lower impedance threshold provides earlier warning for high voltage lead fractures. Heart Rhythm 8:S19, 2011). Similarly, the range of impedance for pace-sense leads can vary widely. A second explanation is that impedance is determined primarily by body tissue, so that even if an in-pocket insulation failure is present, a test pulse delivered from housing to the affected electrode may not detect the insulation failure unless dielectric breakdown is complete.

The difficulty in detecting an insulation failure with present electrical testing may be appreciated from this example. Consider a fracture in the conductor leading to the SVC coil (SVC conductor). Such a fracture—in its initial stages—may have an impedance (to the body core) of 2 kΩ or more. The typical SVC coil has an impedance on the order of 60Ω Thus the parallel combination of the normal impedance and the "leakage" impedance (from the fracture) would result in an impedance reduction of 1.8Ω which is far lower than the typical (5-10Ω) serial impedance changes seen chronically. Similar difficulties are seen with insulation failures on pace/sense conductors as the tip and ring impedances change significantly with fibrosis and other chronic effects.

In the circuit being measured, most of the resistance is at the electrode-tissue interface of the high-resistance tip electrode, and variations of up to 10% in this value are common. Each individual pace-sense conductor (for example, the conductor to the tip electrode or the ring electrode) contributes less than 10% to the measured resistance. In some ICD leads, this value is less than 3%. Thus even if the resistance in a single conductor doubled or tripled, the overall measured resistance will remain within the expected range. Measurements indicate that resistance exceeds the expected range until the conductor has lost most of its structural integrity.

Thus, resistance remains within the expected range even when only a fraction of the conductor is intact. For this reason, resistance measurements are insensitive to partial loss of conductor integrity. Further, resistance measurements have limited specificity. A single, out-of-range value may be an artifact, and marked increases can occur at the electrode-myocardial interface.

In addition to limited sensitivity, present methods for diagnosing lead conductor anomalies have limited specificity resulting in false positive diagnostics. Evaluation of false positive diagnostics adds cost and work to medical care and may contribute to patient anxiety. If a false-positive diagnostic is not diagnosed correctly, patients may be subject to unnecessary surgical lead replacement with its corresponding risks. In the only report on this subject, 23% of leads extracted for the clinical diagnosis of lead fracture tested normally after explant.

Any clinical method for detecting conductor anomalies in implanted leads must make measurements while the conductor and lead are in the body. Typically, the measuring circuit includes the conductor-tissue interface in the body. Thus the measured values will depend both on the behavior of the conductor being evaluated and the conductor-tissue interface.

Existing technology for diagnosis of conductor anomalies in an implantable medical device is believed to have significant limitations and shortcomings. What is desired are method and apparatus that could analyze and identify implantable cardiac lead conductor anomalies at the subclinical stage, before they present as a clinical problem, and do so with a high sensitivity and specificity that minimizes false positives for implantable cardiac lead conductor anomalies.

SUMMARY OF THE INVENTION

The disclosed method and apparatus relates to the diagnosis of conductor anomalies, such as insulation failures, in an implantable medical device, such as an implantable cardioverter defibrillator (ICD), a pacemaker, or a neurostimulator. Insulation failures are detected and localized by identifying changes in electrical fields via surface (skin) potentials. Small variations in potential are detected along the course of the electrode near the site of insulation failure. Pulses delivered to the affected conductor result in the appearance of local electrical equipotential lines, further resulting in a disturbance of local potentials recorded within the body or on the body surface via electrodes on the skin.

One embodiment is a detection method for an insulation failure of a pacing conductor. An insulation failure is checked for in either the tip pacing-sensing electrode or the ring pace-sense electrode. Low amplitude test pulses with short duration<1.5 ms are delivered in a "bipolar" fashion between the "tip" sense conductors and the "ring" sense conductors. Pulses may be delivered in the absolute refractory period after a paced or conducted beat and use a higher output at pulse generator change with background electrical noise. Due to the dipole effect of the closely-spaced "tip" pacing-sensing electrode and "ring" pacing-sensing electrode, the electrical potential lines are tightly located near these electrodes if the insulation around the conductors is intact.

An embodiment is disclosed for detecting an insulation failure in either the tip or ring conductor. In operation, a single recording electrode is moved along the surface of the body parallel to the path of the implanted lead. Another embodiment can utilize multiple simultaneous recordings on the surface of the body, e.g., one over the surgical pocket and intravascular/intracardiac course of the lead. Another embodiment can utilize an array of electrodes deployed in fixed positions over the surface of the body. Further, although the embodiments described utilize the ICD's electronics as the source of test pulses, test pulses may also be delivered at pulse generator change using an external test device such as a programmer.

In this embodiment, the patient is connected to a high-fidelity ECG unit. The high-fidelity ECG unit reliably displays bipolar transvenous pacing pulses, in order to detect the pacing pulses. The test pulse voltage is reduced below the pacing threshold to minimize pacing. The pacing rate is set to a rate faster than the spontaneous ventricular rate in the asynchronous (VOO mode) to provide more pulses to detect and to avoid most QRS complexes. A cutaneous electrode is moved along the surface of the body parallel to the path of the implanted lead. A local maximum voltage spike is searched for. If a local spike, of sufficient amplitude (e.g. >1 mV) is located sufficiently far away from the tip of the lead then an insulation break is indicated.

An embodiment is disclosed for detecting an insulation failure in defibrillation conductors in dual-coil systems. The ICD delivers a continuous high-frequency AC impedance test between the SVC and RV electrodes with the ICD housing turned off. The patient is connected to a high-fidelity ECG unit to detect the pacing pulses. The impedance testing high-frequency signal is turned on by initiating an impedance test. An electrode is moved along the surface of the body parallel to the path of the implanted lead. A local maximum voltage spike is searched for. If a local spike, of sufficient amplitude is located sufficiently far away from the tip of the lead then an insulation break is indicated.

An embodiment is disclosed for detecting an insulation failure in defibrillation conductors in single-coil systems. The ICD is modified to deliver a continuous high-frequency AC impedance test between the RV electrodes and the ICD housing. The patient is connected to a high-fidelity ECG unit to detect the pacing pulses. The impedance testing high-frequency signal is turned on by initiating an impedance test. An electrode is moved along the path of the implanted lead and a local voltage null is searched for. Without any insulation break, there should be a large signal near the ICD can and a large signal near the RV coil. The voltage of this signal is expected to gradually decrease when moving from the can to the RV coil with a polarity inversion (and now voltage null) in between. If a local spike (away from the coil) is located then an insulation break is detected.

In an embodiment, localization of the failure where the insulation failure is adjacent to the ICD housing is disclosed. Pulses or a continuous high-frequency alternating current are delivered over the three current paths corresponding to the three electrodes on the lead which include the pace-sense (tip-ring) dipole, the ring-RV coil dipole, and the tip-RV coil dipole. In no case should there be evidence of current flow near the pocket or directly under the clavicle (clavicular crush). By determining which dipole or dipoles do not result in an anomalous potential near the housing, identification of the remaining conductor can be made as having failed insulation.

Another embodiment for localizing an insulation break is disclosed. Localization of the break can be accomplished via a high-resolution inverse-ECG system that is modified to provide potentials along the path of the lead with the suspected insulation break. The method is performed by modifying inverse-ECG system to calculate potentials along the lead. The next step is connecting the patient to the inverse-ECG system and then delivering pacing or AC impedance test stimuli. The steps further include locating maximum signals that are not at an electrode and localizing the insulation break to the region of maximum signal that are not adjacent to a stimulated electrode.

In an embodiment, the test signals as generated in the embodiments of the methods about are generated from an implantable pulse generator. In another embodiment, an apparatus including an external test device, such as programmer module, is utilized with the implant device. The apparatus has an AC amplifier, an AC generator, a filter, a modulator and a digital meter. In an embodiment, the AC generator is configured to deliver a sine wave to the implanted leads during a procedure that involves disconnecting the leads from the pulse generator. Typically, this occurs for a device change due to battery depletion or infection. The frequency of the sine wave is chosen so that it is above the frequencies that affect cardiac cells. In embodiments, a voltage of is delivered to give a strong signal at the skin surface.

In an embodiment, a number of ECG adhesive electrodes would be placed in the region of the implantable lead and be connected to a switch-box. The operator would then select the desired electrode, one at a time. The "reference" electrode would be a subcutaneous electrode in the device pocket. As the clinician moves the roving electrode, via the switch-box, the digital meter displays the signal at each skin location and is thus able to find the skin location with the strongest signal.

BRIEF DESCRIPTION OF THE DRAWINGS

The invention may be more completely understood in consideration of the following detailed description of various embodiments of the invention in connection with the accompanying drawings, in which:

FIG. 2B is a cross-sectional view of the Medtronic Sprint Fidelis® Lead, a multi-lumen ICD implantable cardiac lead.

Figure 1:
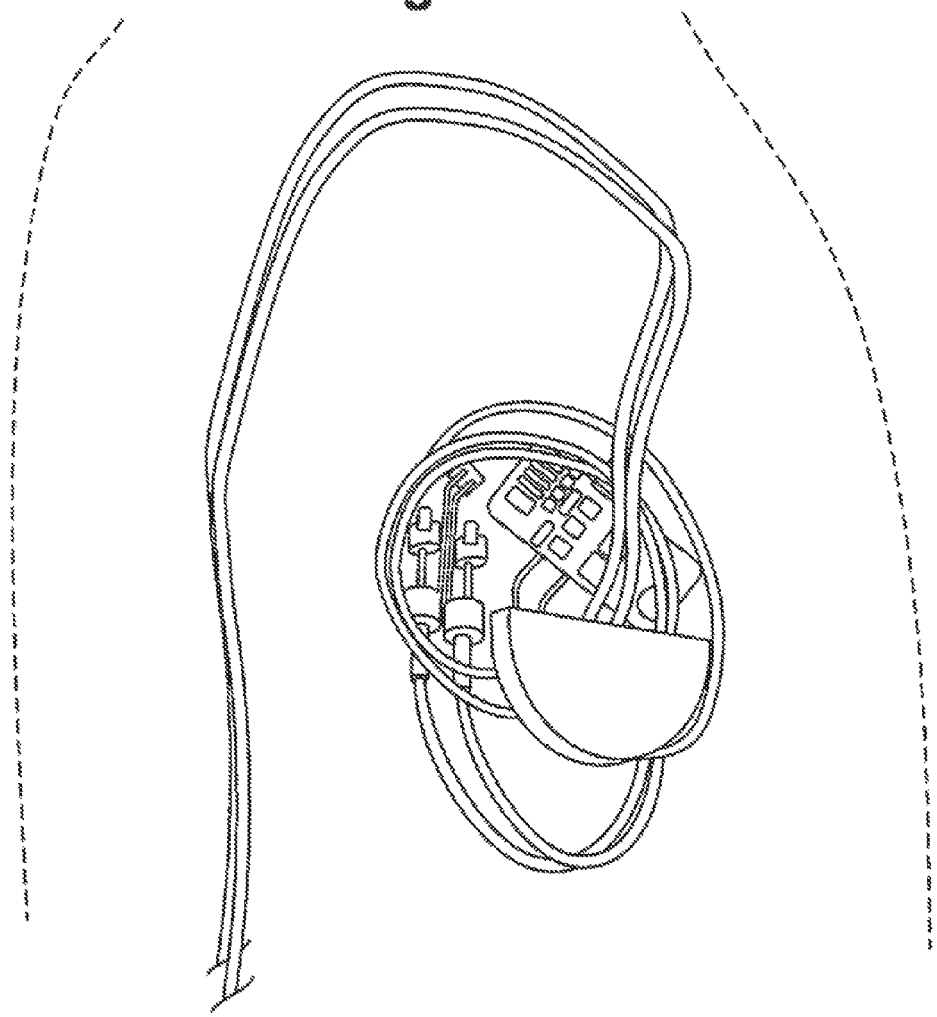
FIG. 1 shows a radiograph or x-ray of an implantable cardioverter defibrillator (ICD) implanted in a human body where the lead has a small area of insulation stress from a tight suture.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The embodiments herein are directed to the diagnosis of lead or conductor anomalies, such as insulation failures, in an implantable medical device, such as pacemakers, vagal nerve stimulators, pain stimulators, neurostimulators, and implantable cardioverter defibrillators (ICDs). However, for clarity, discussion of lead or conductor anomalies will be made in reference to ICDs. However, those with skill in the art are cognizant of the fact that the methods and apparatus as disclosed herein are suitable for use with any one of the various implantable medical devices.

Figure 2A:
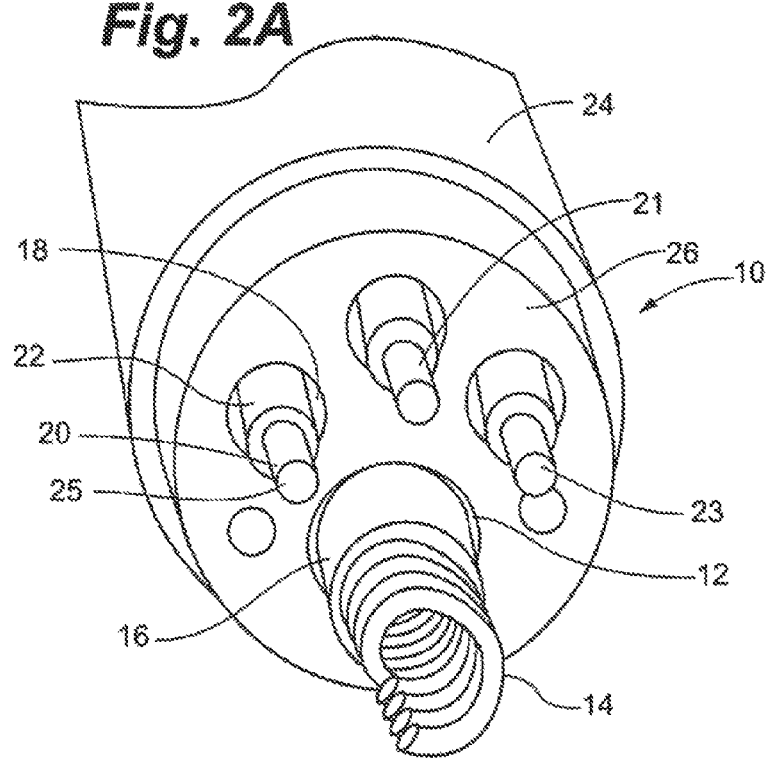
FIG. 2A is a cross-sectional view of the Medtronic Quattro Secure® Lead, a multi-lumen ICD implantable cardiac lead.
Figure 3:
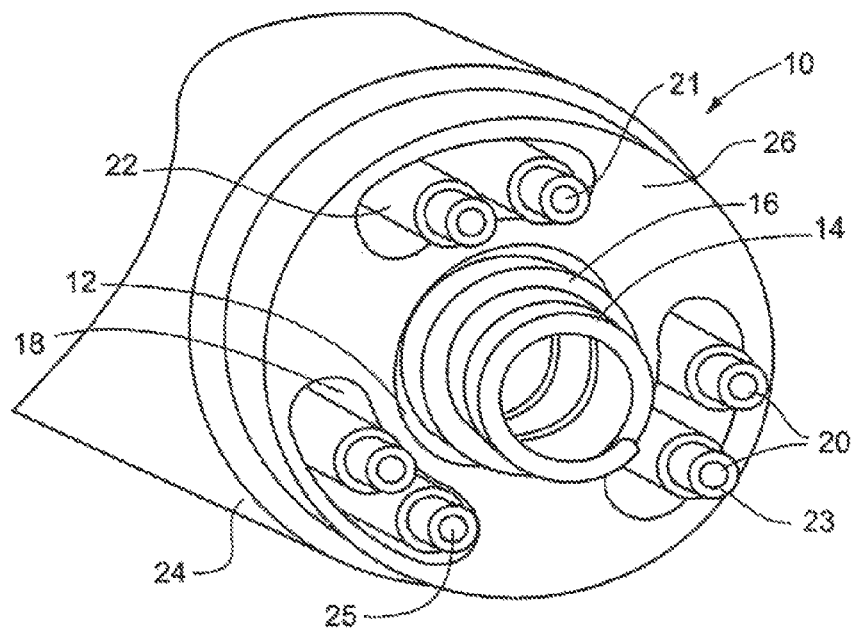
FIG. 3 is a cross-sectional view of the St. Jude Medical Riata® Lead, a multi-lumen ICD implantable cardiac lead.

FIGS. 2A, 2B and 3 depict known multi-lumen ICD defibrillation electrodes or leads that have been diagnosed with lead conductor anomalies. While these are indicative of the type of leads that can be diagnosed, anomalies in any type of defibrillation electrodes or leads are capable of being diagnosed with the methods and apparatus as disclosed herein. FIG. 2A depicts the Medtronic Quattro Secure® Lead. FIG. 2B depicts the Medtronic Sprint Fidelis® Lead. FIG. 3 depicts the St. Jude Medical Riata® Lead. The leads 10, while having various constructions, have similar features. These similar features are identified with the same reference numbers in the figures.

The implantable cardiac lead 10 is comprised of a lumen 12 and center inner pacing coil 14 surrounded by PTFE insulation 16, a plurality of lumens 18 each containing at least one conductor 20 with each conductor 20 surrounded by ETFE insulation 22, an outer insulating layer 24, and a silicone insulation 26 disposed between the lumen 12 and the outer insulating layer 24. The conductors 20 include a sense conductor 21, a high voltage RV conductor 23 and a high voltage SVC conductor 25. The plurality of lumens 18 are disposed in the silicone insulation 26. The conductors 20 carry electric current to the pace-sense electrodes 66, 68, high voltage RV coil 64 and high voltage SVC coil 62.

Figure 4:
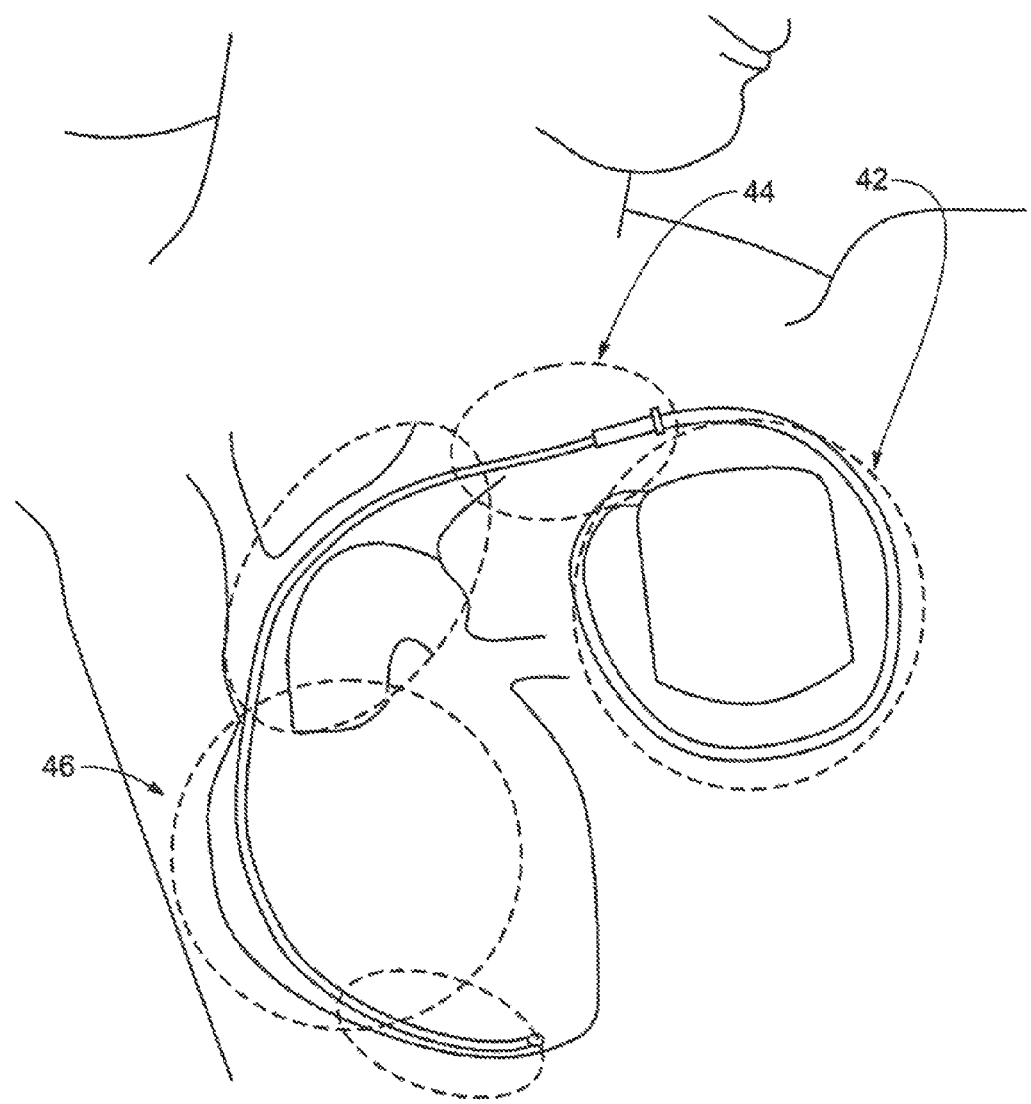
FIG. 4 illustrates regions within the human body associated with the implantation of an ICD and associated leads.

As discussed above, and shown in FIG. 4, insulation failures most commonly occur at three regions along the course of a pacemaker or ICD lead 10. The first region 42 is proximate the pocket, caused either by abrasion of the lead 10 insulation 24 by pressure from the housing ("CAN") of the pulse generator or twisting of the lead 10 within the pocket. The second region 44 is that between the clavicle and first rib, where the lead 10 is subject to "clavicular crush." The third region 46 is the intracardiac region near the tricuspid valve. This third region 46 is a particularly common site of insulation 24 failure for the St. Jude Riata® lead 10 which is subject to "inside-out" insulation failure due to motion of the internal conductors 20 relative to the outer insulation 24.

Figure 5:
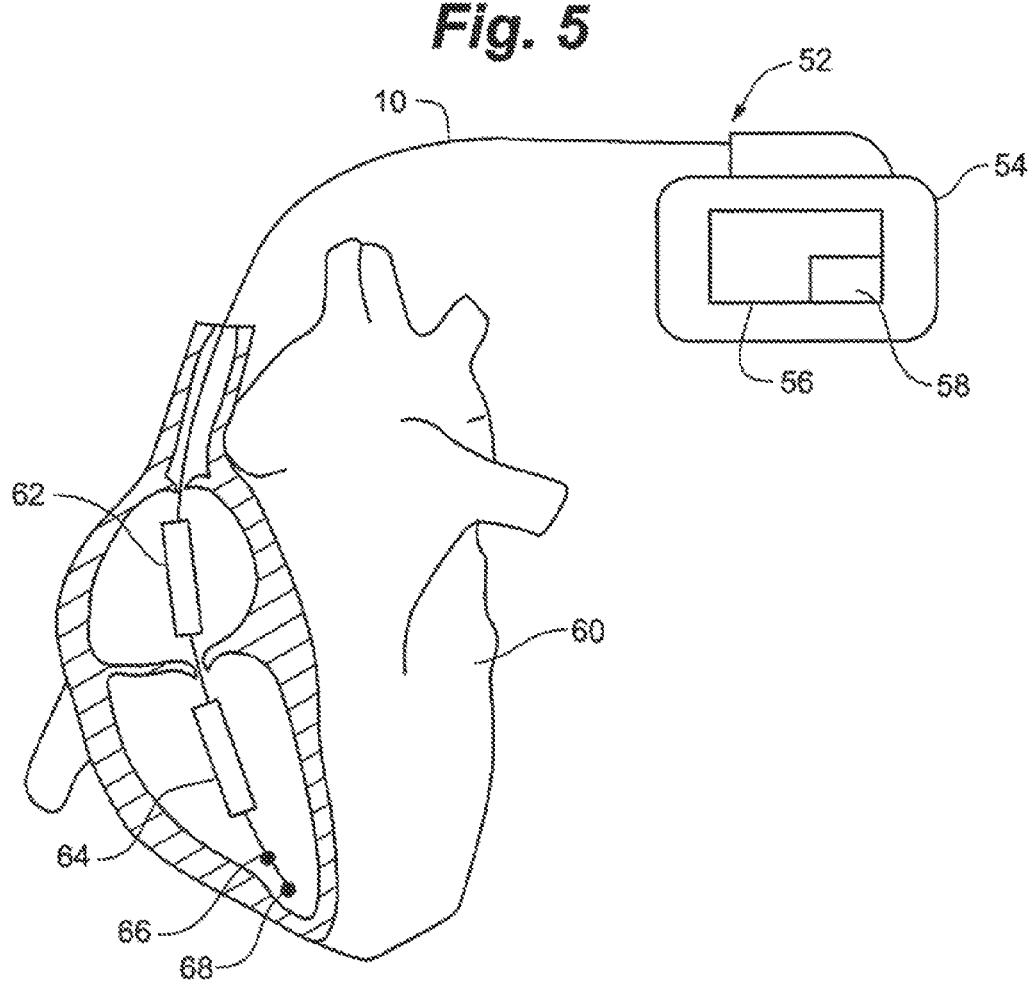
FIG. 5 shows an implantable medical device in which an embodiment of the present invention may be practiced. It shows an ICD pulse generator connected to a patient's heart via a transvenous cardiac lead used for pacing and defibrillation.

FIG. 5 depicts on ICD 52 implanted in the chest of a patient. The ICD 52 has an outer housing 54, commonly referred to as a "CAN," inner circuitry 56 and a battery 58. Connection is made to the heart 60 via the lead 10. The lead 10 can have an optional proximal defibrillation coil 62 which is near the superior vena cava (SVC) and is commonly referred to as the SVC coil 62. The lead 10 also has a distal defibrillation coil 64 which is commonly referred to as the right-ventricular coil or RV coil 64. Also shown is the optional "ring" pacing-sensing electrode 66. Located at the distal end of the lead 10 is the "tip" pacing-sensing electrode 68.

The outer insulating layer 24 of the leads 10 is generally a polymer such as silicone, polyurethane, or a copolymer of silicone and polyurethane. Stress on the insulation 24 from anchoring sutures, outside-in abrasion from contact with the housing, or inside-out abrasion from movement of the cables within the lead 10 may result in insulation 24 breaches or failures. In addition, the insulation 24 can fail due to chemical reactions such as metal-ion oxidation.

Figure 6:
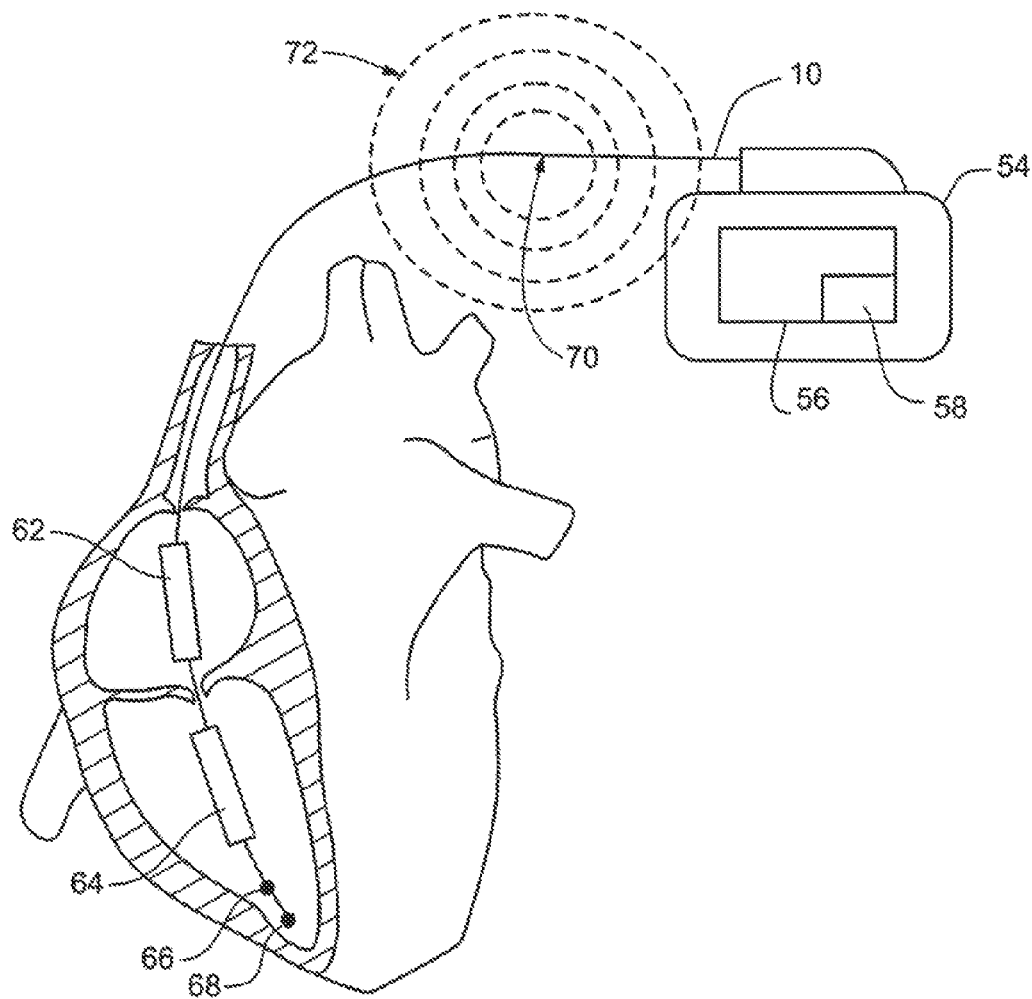
FIG. 6 shows an ICD pulse generator connected to a patient's heart via a transvenous cardiac lead used for pacing and defibrillation where the lead contains an insulation failure nearer the ICD.

FIG. 6 depicts a lead 10 insulation 24 failure at location 70. When pulses are delivered to the affected conductor 20 the local electrical equipotential lines appear approximately as those shown at 72. This results in a disturbance of local potentials recorded within the body or on the body surface via electrodes on the skin.

Figure 7:
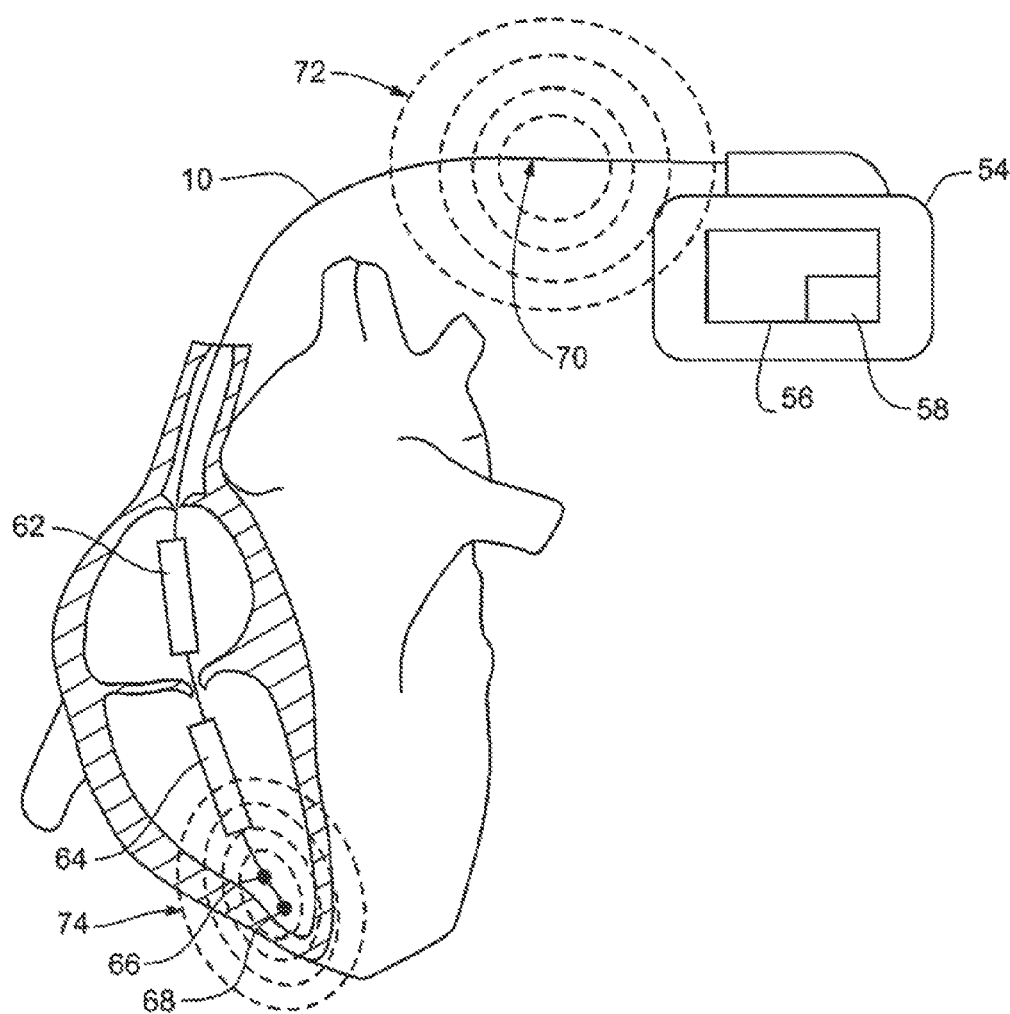
FIG. 7 shows an ICD pulse generator connected to a patient's heart via a transvenous cardiac lead used for pacing and defibrillation where the lead contains an insulation failure nearer the ICD and the method of checking for failure in either the tip or ring pace-sense conductors.

FIG. 7 depicts an example of a detection method for pacing conductors 14. In this embodiment, an insulation failure is checked for in either the tip pacing-sensing electrode 68 or the ring pace-sense electrode 66. Low amplitude (<1 V) test pulses with duration<1.5 ms are delivered in a "bipolar" fashion between the "tip" sense conductors 21 and the "ring" sense conductors 21. Pulses may be delivered in the absolute refractory period after a paced or conducted beat. The test pulse may be delivered, under sedation in a surgical suite, using a higher output at pulse generator change with background electrical noise. Due to the dipole effect of the closely-spaced "tip" pacing-sensing electrode 68 and "ring" pacing-sensing electrode 66, the electrical potential lines are tightly located near these electrodes 66, 68 if the insulation around the conductors is intact, as shown by the smaller ovals 74. Note that these ovals in FIG. 7 represent a simplification of the actual equi-potential lines which are typically positive (+) around the "ring" pacing-sensing electrode 66 and negative (−) around the "tip" pacing-sensing electrode 68.

The amplitude of the skin-surface potential during bipolar pacing is on the order of approximately 1 mV in a conventional lead and much weaker in other locations with high-fidelity ECG units. An example of a high-fidelity ECG unit is the GE MAC 5500 HD. Due to the high-frequency nature of the pacing pulse it is typically invisible on older ECG units due to their low-pass filtering.

Figure 8:
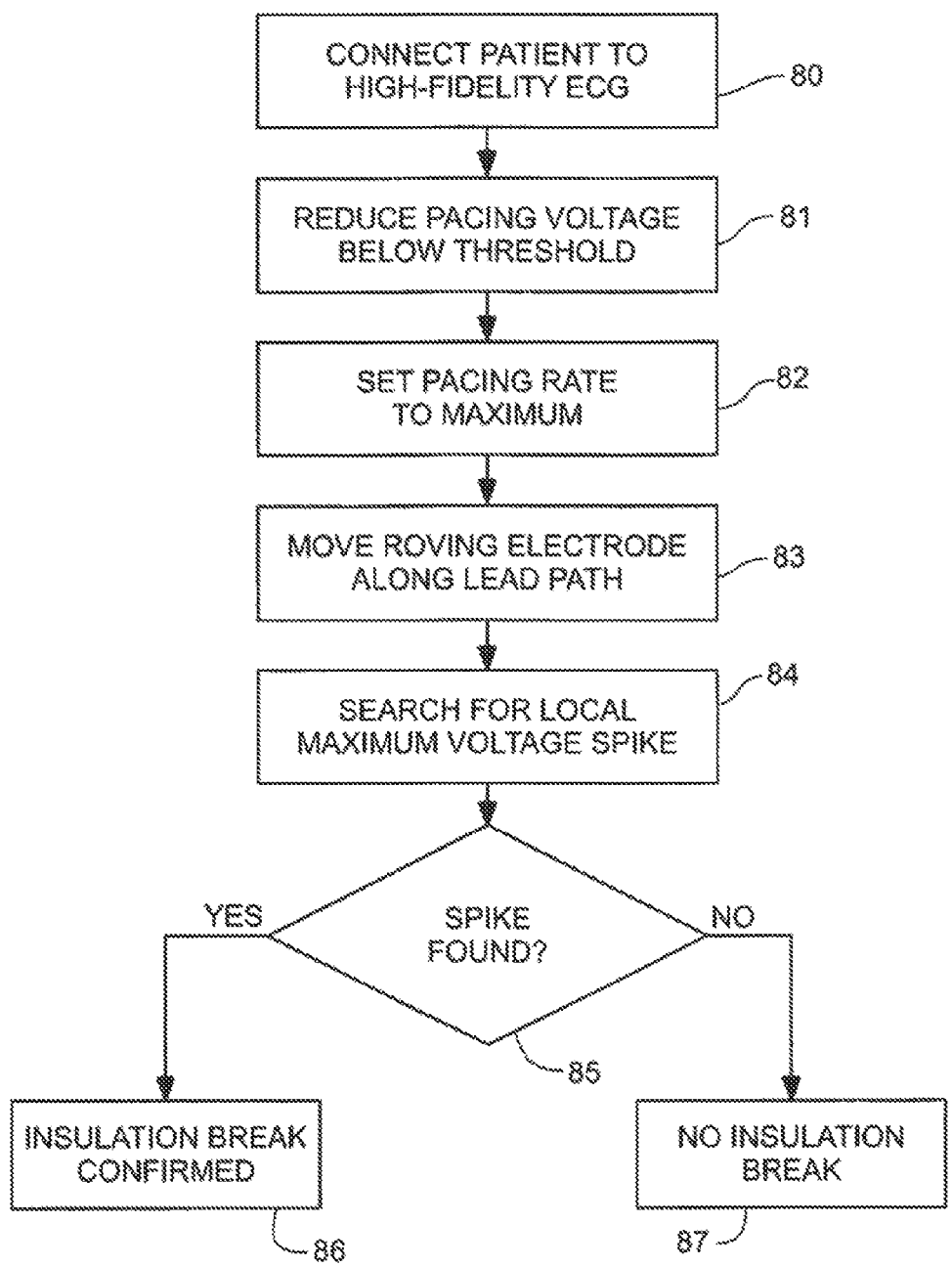
FIG. 8 is a flowchart depicting the method of detecting an insulation failure in either the tip or ring pacing conductor.

FIG. 8 depicts an embodiment of a method for detecting an insulation failure in either the tip or ring conductor 20. Note that this method is able to be used for any pacing conductor such as endocardial electrodes in the right atrium, coronary sinus, or the left ventricle, as well as epicardial or subcutaneous electrodes. In operation, a single recording electrode is moved along the surface of the body parallel to the path of the implanted lead 10. Visual confirmation of the path can be provided by, for example, radiographic methods, such as an x-ray taken in one or more views, or by CT scan. Another embodiment can utilize multiple simultaneous recordings on the surface of the body, e.g., one over the surgical pocket and intravascular/intracardiac course of the lead 10. Another embodiment can utilize an array of electrodes deployed in fixed positions over the surface of the body. Further, although the embodiments described utilize the ICD's 52 electronics 56 as the source of test pulses, test pulses may also be delivered at pulse generator change using an external test device such as a programmer.

The method shown in FIG. 8 connects the patient to a high-fidelity ECG unit 80. The high-fidelity ECG unit reliably displays bipolar transvenous pacing pulses, in order to detect the pacing pulses. The test pulse voltage is reduced below the pacing threshold 81 to minimize pacing. The pacing rate is set to a rate faster than the spontaneous ventricular rate 82 in the asynchronous (VOO mode) to provide more pulses to detect and to avoid most QRS complexes.

A cutaneous electrode is moved along the surface of the body parallel to the path of the implanted lead 83. Visual confirmation of the path can be provided by, for example, radiographic methods, such as an x-ray taken in one or more views, or by CT scan. The cutaneous electrode movement includes the loops of lead in the pocket which is a common site of insulation breach. A local maximum voltage spike is searched for 85. If a local spike, of sufficient amplitude (e.g. >1 mV) is located sufficiently far away from the tip of the lead then an insulation break is detected 86. Else, an insulation break is not detected 87. If the patient cannot tolerate a brief absence of pacing, then pacing is performed at a rate between the lower and upper rate limits (inclusive) with the voltage set to the maximum.

Figure 9:
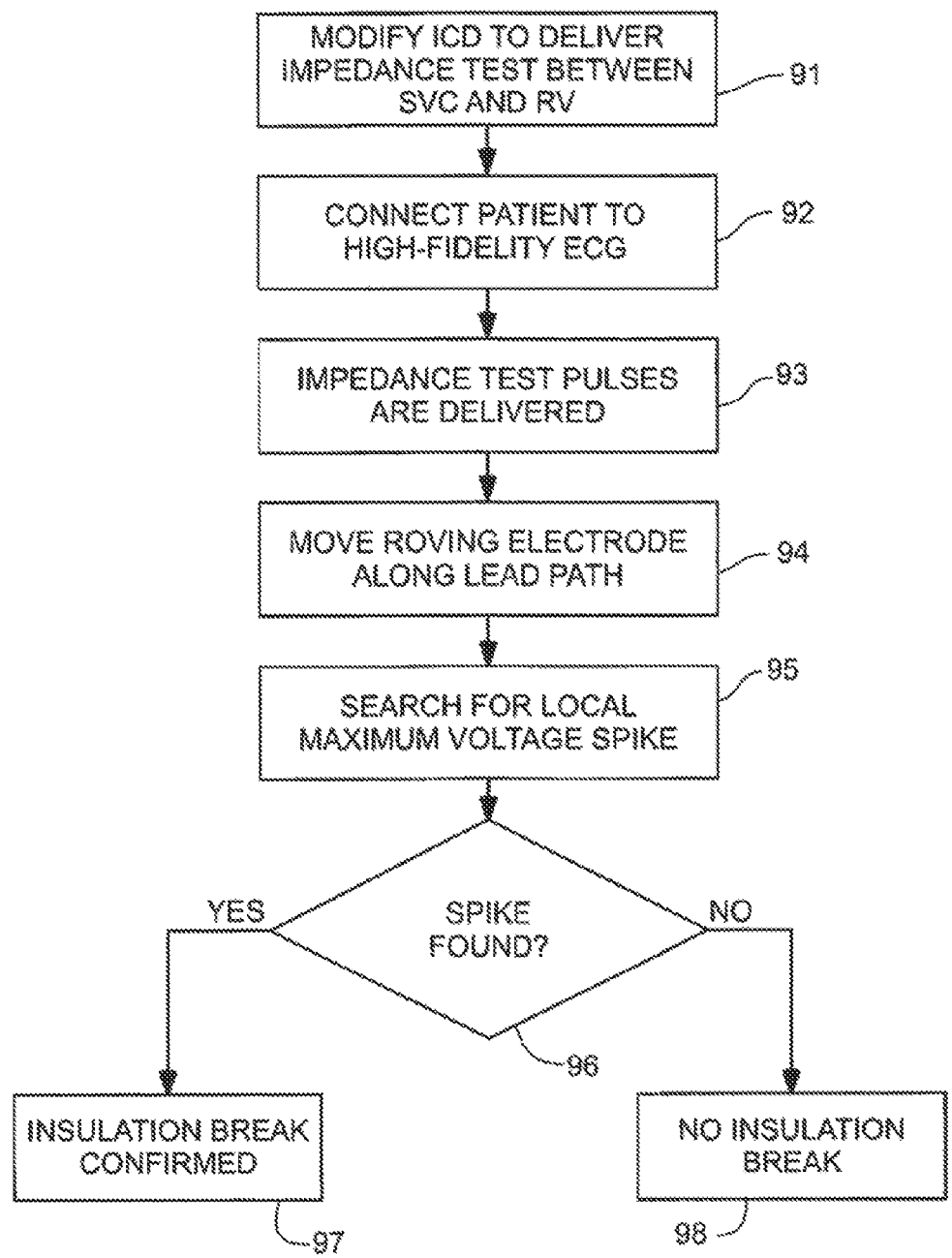
FIG. 9 is a flowchart depicting the method of detecting an insulation failure in defibrillation conductors in dual-coil systems.

FIG. 9 depicts an embodiment of a method for detecting an insulation failure in defibrillation conductors in dual-coil systems. The method can detect a possible insulation break in either one of the defibrillation conductors. The ICD is modified to deliver a continuous high-frequency AC impedance test between the SVC and RV electrodes with the ICD housing turned off 91. The patient is connected to a high-fidelity ECG unit 92 such as a GE MAC 5500 HD in order to detect the pacing pulses. The impedance testing high-frequency signal is turned on by initiating an impedance test 93. An electrode is moved along the surface of the body parallel to the path of the implanted lead 94. Visual confirmation of the path can be provided by, for example, radiographic methods, such as an x-ray taken in one or more views, or by CT scan. The electrode movement includes the loops of lead in the pocket which is a common site of insulation breach. A local maximum voltage spike is searched for as shown at 95. If a local spike, of sufficient amplitude is located sufficiently far away from the tip of the lead then an insulation break is detected as shown at 97. Else, an insulation break is not detected as shown at 98.

Figure 10:
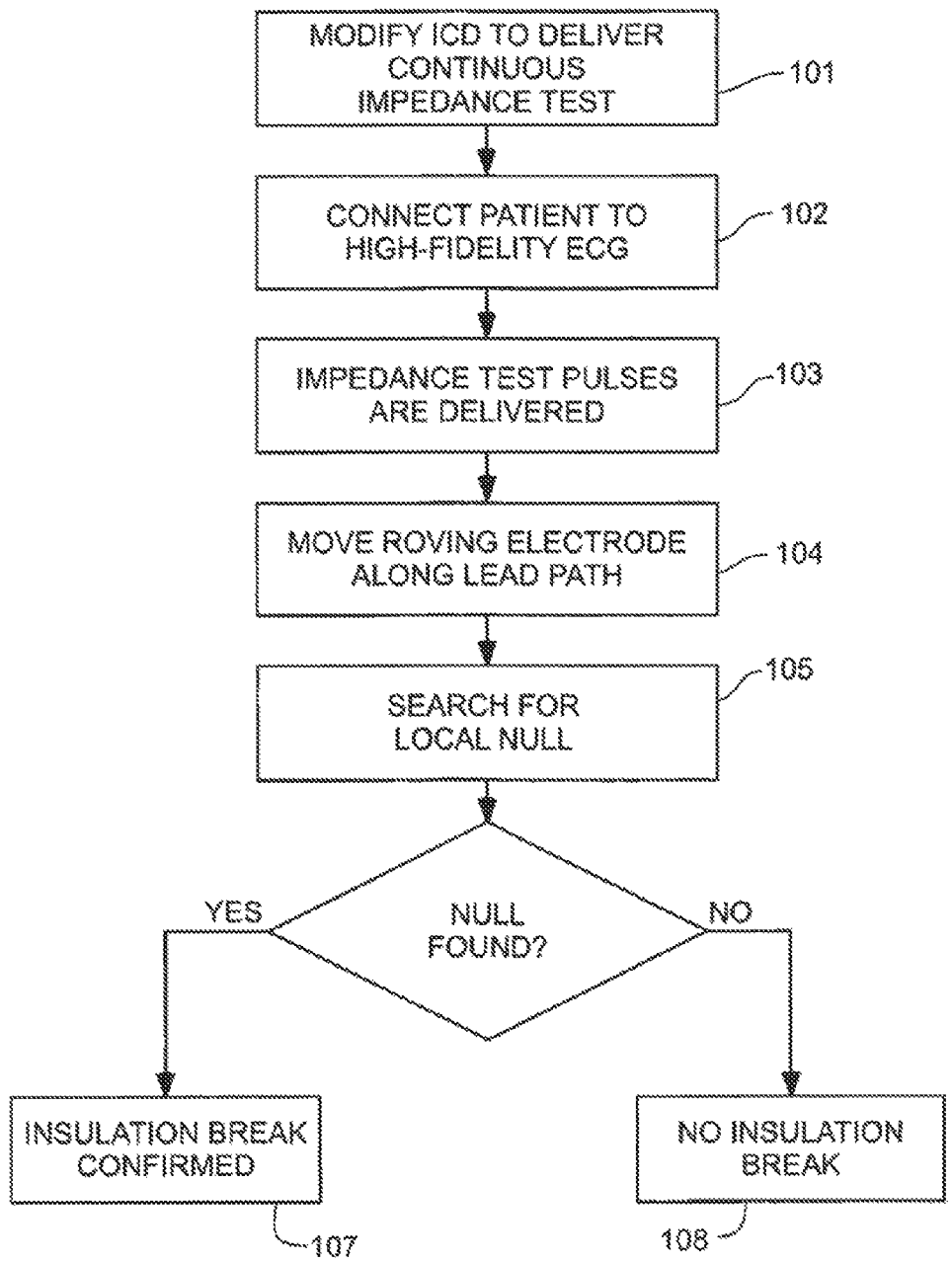
FIG. 10 is a flowchart depicting the method of detecting an insulation failure in defibrillation conductors in single-coil systems.

FIG. 10 depicts an embodiment of a method for detecting an insulation failure in defibrillation conductors in single-coil systems. The method can detect a possible insulation break in either one of the defibrillation conductors. The ICD is modified to deliver a continuous high-frequency AC impedance test between the RV electrodes and the ICD housing 101. The patient is connected to a high-fidelity ECG unit 102 such as a GE MAC 5500 HD in order to detect the pacing pulses. The impedance testing high-frequency signal is turned on by initiating an impedance test 103. An electrode is moved along the path of the implanted lead 104. Visual confirmation of the path can be provided by, for example, radiographic methods, such as an x-ray taken in one or more views, or by CT scan. A local voltage null is searched for at 105. Without any insulation break, there should be a large signal near the ICD can and a large signal near the RV coil 108. The voltage of this signal is expected to gradually decrease when moving from the can to the RV coil with a polarity inversion (and now voltage null) in between. If a local spike (away from the coil) is located then an insulation break is detected at 107. Else, an insulation break is not detected at 108.

In the case of an insulation 24 failure adjacent to the ICD's 52 housing 54, it is sometimes difficult to localize the failure using the above techniques of detecting a surface potential. In this type of scenario, pulses or a continuous high-frequency alternating current are delivered over the three current paths corresponding to the three electrodes on the lead which include the pace-sense (tip-ring) dipole, the ring-RV coil dipole, and the tip-RV coil dipole. In no case should there be evidence of current flow near the pocket 42 or directly under the clavicle (clavicular crush) 44. By determining which dipole or dipoles do not result in an anomalous potential near the housing, identification of the remaining conductor can be made as having failed insulation 24.

Figure 11:
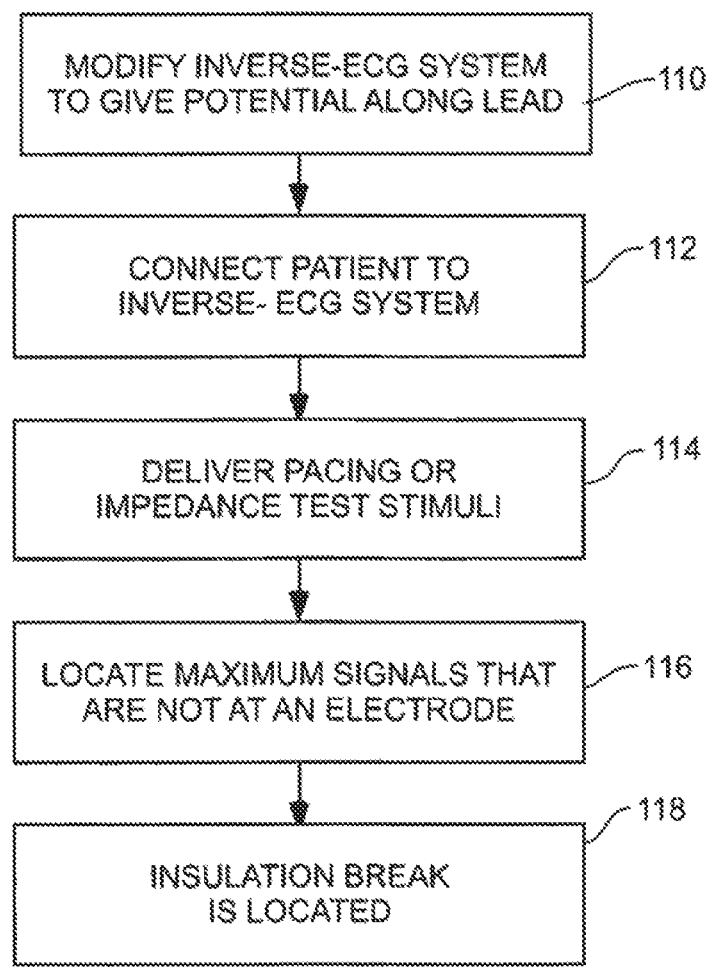
FIG. 11 is a flowchart depicting the method of localizing an insulation failure.

FIG. 11 depicts a method of localizing an insulation break. Once an insulation break is detected or indicated, localization of the break can be accomplished via a high-resolution inverse-ECG system such as the Cardio-Insight mapping system. The method requires that the system be modified to provide potentials along the path of the lead with the suspected insulation break. The method is performed by modifying inverse-ECG system to calculate potentials along the lead 110. The next step is connecting the patient to the inverse-ECG system 112 and then delivering pacing or AC impedance test stimuli. The steps further include locating maximum signals that are not at an electrode 116 and localizing the insulation break to the region of maximum signal that are not adjacent to a stimulated electrode.

Additionally, for the embodiments as disclosed herein, a baseline recording (or set of recordings) can be completed when the lead system becomes stable, which is typically between one and three months after implant. The sites of maximum potential in subsequent testing may then be compared with sites of maximum potential during subsequent testing either by the operator or by using custom software.

The above descriptions depict the duration of the testing process as an embodiment of a single test setting (e.g. at pulse generator change or in out-patient follow up). However, in other embodiments, the methods can be practiced with a 24 hour to one week ambulatory recording period thus providing an extended time period that can be used to effectively identify intermittent lead insulation failure. In embodiments, the recording system may be activated by telemetry signals delivered by the pulse generator.

Figure 12:
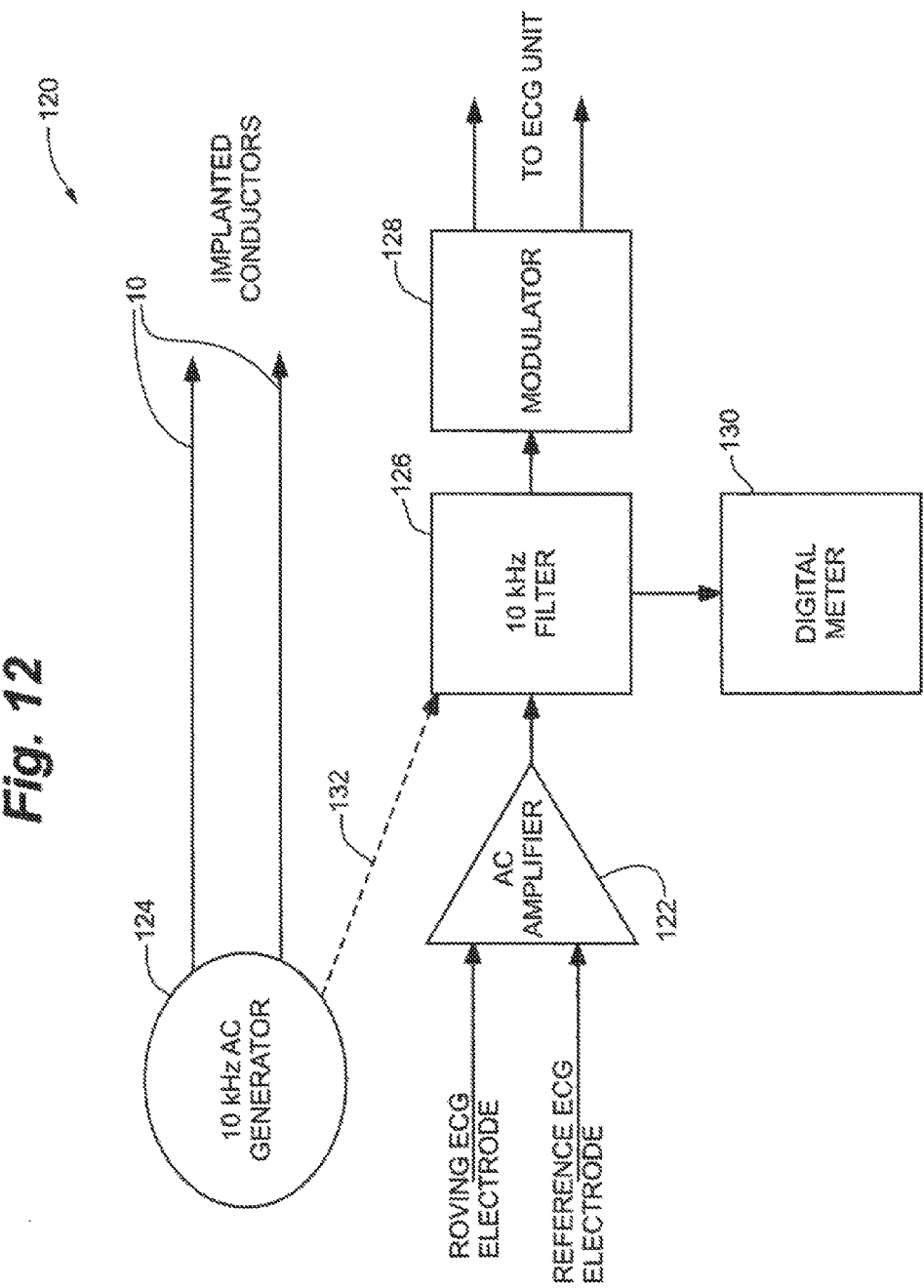
FIG. 12 illustrates an apparatus used to generate test signals and display the amplified signal amplitude.

In an embodiment, the test signals as generated in the embodiments of the methods about are generated from an implantable pulse generator. In another embodiment, as shown in FIG. 12, an apparatus including an external test device, such as programmer module, is utilized at implant. and measurements from the cutaneous electrodes are analyzed in near real time using the external test device. The apparatus 120 has an AC amplifier 122, an AC generator 124, a filter 126, a modulator 128 and a digital meter 130. One input of the AC amplifier is connected to the roving ECG electrode and the other input is connected to the reference ECG electrode. The AC amplifier output is fed into the filter 126, which is depicted as a 10 kHz filter but it is not so limited. The filter 126 is output to the modulator 128 and to the digital meter 130. The AC generator 124 is connected to the implanted leads. The AC generator 124 is depicted as a 10 kHz AC generator but it is not so limited. Additionally the AC generator 124 is connected to the filter 126.

In an embodiment, the test pulses are delivered through the implanted pulse generator. Measurements from the cutaneous electrodes are then stored in an ambulatory recording device or long-term electrocardiographic event recorder. In some embodiments, the recording device can be equipped with a larger electrode array as described herein with respect to other embodiments. After a specified monitoring period, e.g., 24 hour to one week to one month or longer ambulatory recording period, the stored measurements are downloaded to an external analysis unit. In embodiments, the recording system may be activated by telemetry signals delivered by the pulse generator. It is apparent to those skilled in the art that the ambulatory recording period can be any timeframe as specified by the physician that is sufficient to accomplish the purposes herein.

In an embodiment, the 10 kHz AC generator 124 is configured to deliver a 10 V sine wave to the implanted leads 10 during a procedure that involves disconnecting the leads 10 from the pulse generator. Typically, this occurs for a device change due to battery depletion or infection. The 10 kHz frequency is chosen as it is above the frequencies that affect cardiac cells. In certain embodiments, frequencies of 5 to 25 kHz are used but, in other embodiments, frequencies of 1 to 250 kHz can be used. Care should be taken at lower frequencies because cardiac capture or collapse can occur with sufficient amplitudes. In embodiments, a voltage of 5 V AC is delivered to give a strong signal at the skin surface. In other embodiments, voltages of 1 to 20 V AC are provided.

In an embodiment, the signal from the recording electrode or electrodes is fed thru the amplifier 122 and then filtered by a narrow-band filter 126. The filter 126 can be either an analog or digital notch filter. On another embodiment, the filter can be a synchronous filter using the signal 132 for synchronization from the generator 124. Extremely high signal-to-noise ratios are thus achieved. The generator frequency and the filter frequency should be the same.

In this embodiment, the roving electrode would not be physically moved. Rather, a number of ECG adhesive electrodes would be placed in the region of the implantable lead 10 and be connected to a switch-box. The operator or a computerized system would then select the desired electrode, one at a time. The "reference" electrode would be a subcutaneous electrode in the device pocket 42.

The amplified signal is then modulated down to a lower frequency, e.g., 100 Hz, so that the signal can be readily processed by a conventional ECG unit. The digital meter 130 displays the amplified signal amplitude. As the clinician moves the roving electrode, via the switch-box, the digital meter 130 displays the signal at each skin location and is thus able to find the skin location with the strongest signal. Additionally, an ECG unit is not required as the digital meter 130 displays the signals.

In an alternative embodiment, the signal generator generates a 90 Hz sine wave which is easy to differentiate from utility 50/60 Hz interference and has the advantage of passing readily thru any ECG unit. It does have the disadvantage of limited driving voltage as such frequencies can easily cause cardiac collapse.

The following patents and applications, the disclosures of which are incorporated by reference in this case (other than claims and express definitions), are prior art attempts by common inventors to solve the problem at issue: U.S. Pat. No. 8,352,033 (033) to Kroll, issued Jan. 8, 2013; U.S. patent application Ser. No. 13/735,599 to Kroll, filed on Jan. 7, 2013 which is a continuation of '033; and U.S. patent application Ser. No. 12/868,056 to Swerdlow, filed on Aug. 25, 2010.

The following provisional applications, the disclosures of which are incorporated by reference in this case (other than claims and express definitions), are related to each other: U.S. Patent Application 61/689,191 to Kroll and Swerdlow, filed on Jun. 1, 2012; U.S. Patent Application 61/689,189 to Kroll and Swerdlow, filed on Jun. 1, 2012; and U.S. Patent Application 61/733,713 to Kroll and Swerdlow, filed on Dec. 5, 2012.

The values noted above are example embodiments and should not be read as limiting the scope of this invention.

Those skilled in the art will recognize that the above values may be adjusted to practice the invention as necessary depending on the electrode implantable cardiac lead technology used and the physical characteristics of the patient.

While the present invention has been described with reference to certain embodiments, those skilled in the art should appreciate that they can readily use the disclosed conception and specific embodiments as a basis for designing or modifying other structures for carrying out the same purposes of the present invention without departing from the spirit and scope of the invention as defined by the appended claims.

The invention claimed is:

1. A method for detecting an insulation failure of an implantable defibrillation lead, the defibrillation lead connected to an implanted electromedical device and in electrical communication with a heart of a patient comprising:
   delivering at least one low amplitude test electrical pulse that is below a pacing threshold having a pacing rate faster than a spontaneous ventricular rate through at least one conductor in the defibrillation lead;
   recording an electrical potential at recording sites, said recording sites being located at one or more body locations spaced apart from and relative to a path of the defibrillation lead;
   wherein recording said electrical potential is accomplished via a single roving electrode placed sequentially at different exterior body surface locations; and
   analyzing said electrical potential recorded from said recording sites to determine a presence of an insulation failure by recognizing a local maximum voltage spike in said electrical potential recorded from said recording sites wherein a local maximum voltage spike is recognized when said electrical potential at one of more of said recording sites is significantly higher than an electrical potential at other recording sites.

2. The method of claim 1 wherein the delivering of at least one test electrical pulse is from the implanted electromedical device.

3. The method of claim 1 wherein the delivering of at least one test electrical pulse is from an external test device.

4. The method of claim 1 wherein the implanted electromedical device is selected from the group consisting of implantable cardioverter defibrillators with transvenous leads, implantable cardioverter defibrillators with subcutaneous leads, vagal nerve stimulators, pain stimulators, pacemakers, and neurostimulators.

5. The method of claim 1 wherein the delivering of at least one test electrical pulse further comprises delivering a plurality of low amplitude test electrical pulses, wherein each of the plurality of low amplitude test electrical pulses are delivered at different voltages.

6. The method of claim 1 wherein a relative change in electrical potentials at different recording sites identifies the presence of the insulation failure.

7. The method of claim 1 wherein the implanted electromedical device is an implantable cardioverter defibrillator and the lead is a multilumen defibrillation lead.

8. The method of claim 7 wherein the at least one test electrical pulse is delivered through at least one pair of conductors, the pair of conductors selected from the group consisting of pace to sense, ring to right-ventricular coil, tip to right-ventricular coil, and right-ventricular coil to superior vena cava coil.

9. The method of claim 1 wherein the at least one test electrical pulse is delivered through a multiplicity of pairs of conductors and the insulation failure is identified by differences in the pattern of recorded electrical potentials.

10. The method of claim 1 wherein the at least one test electrical pulse is delivered through an implanted pulse generator and measurements from cutaneous electrodes are analyzed in near real time using an external test device.

11. The method of claim 1 further comprising:
    delivering the at least one test electrical pulse through an implanted pulse generator;
    storing measurements from cutaneous electrodes in an ambulatory recording device or long-term electrocardiographic event recorder; and
    downloading the stored measurements to an external analysis unit after a monitoring period.

12. The method of claim 11 further comprising activating data storage in the ambulatory recording device via telemetry from the implanted pulse generator.

13. The method of claim 1 further comprising:
    recording a distribution of body surface potentials in response to a plurality of test pulses delivered via various combinations of conductors after implant;
    storing the distribution of body surface potentials as a baseline map;
    recording a subsequent distribution of body surface potentials;
    comparing the subsequent distribution of body surface potentials with the baseline map; and
    identifying an insulation failure relative to the subsequent distribution of body surface potentials differing sufficiently from the baseline map.

14. The method of claim 1, further comprising localizing the insulation failure by:
    modifying a high resolution inverse-ECG system to provide potentials along a path of the implantable lead;
    attaching the inverse-ECG system to the patient;
    delivering pacing or impedance test stimuli;
    locating maximum signals not at an electrode; and
    localizing the insulation break to a region of maximum signal not adjacent to an electrode.

15. A method for detecting an insulation failure of an implantable defibrillation lead, the defibrillation lead connected to an implanted electromedical device and in electrical communication with a heart of a patient comprising:
    delivering at least one low amplitude test electrical pulse that is below a pacing threshold having a pacing rate faster than a spontaneous ventricular rate through at least one conductor in the defibrillation lead;
    recording an electrical potential at recording sites, said recording sites being located at one or more body locations spaced apart from and relative to the path of the defibrillation lead; and
    analyzing said electrical potential recorded from said recording sites to determine a presence of an insulation failure by recognizing a local maximum voltage spike in said electrical potential recorded from said recording sites wherein a local maximum voltage spike is recognized when said electrical potential at one of more of said recording sites is significantly higher than an electrical potential at other recording sites;
    wherein recording the electrical potential is accomplished via one or more electrodes located within the body, the electrodes not being connected to the implantable lead being analyzed for said insulation failure; and wherein the electrodes include:
    an implantable cardioverter defibrillator housing; and
    an electrode temporarily implanted within the surgical pocket.

* * * * *